United States Patent

Ripa et al.

[11] Patent Number: 6,054,581
[45] Date of Patent: *Apr. 25, 2000

[54] PROCESS FOR THE PREPARATION OF 1,4,7, 10-TETRAAZA-CYCLODODECANE-1,4,7-TRIACETIC ACID AND THE DERIVATIVE THEREOF

[75] Inventors: Giorgio Ripa; Alessandro Scala; Marcella Murru; Emanuela Panetta; Carlo Felice Viscardi; Marina Ausonio, all of Milan, Italy

[73] Assignee: Dibra S.p.A., Milan, Italy

[*] Notice: This patent is subject to a terminal disclaimer.

[21] Appl. No.: 09/339,957

[22] Filed: Jun. 25, 1999

Related U.S. Application Data

[62] Division of application No. 09/095,016, Jun. 10, 1998, Pat. No. 5,962,679.

[30] Foreign Application Priority Data

Jun. 11, 1997 [IT] Italy .................................. MI97A1373

[51] Int. Cl.[7] .................................................. C07D 273/00
[52] U.S. Cl. ........................................... 540/474; 540/470
[58] Field of Search ............................................. 540/474

[56] References Cited

U.S. PATENT DOCUMENTS 5,747,000  5/1998  Platzek .................................. 424/9.363
5,925,752  7/1999  Ripa et al. ................................. 540/474
5,962,679  10/1999  Ripa et al. ................................. 540/474

OTHER PUBLICATIONS

Dischino et al, Inorg. Chem., 1991, 20 p. 1267.

*Primary Examiner*—Mukund J. Shah
*Assistant Examiner*—Pavanaram K Sripada
*Attorney, Agent, or Firm*—Nixon & Vanderhye P.C.

[57] ABSTRACT

A process for the preparation of 1,4,7,10-tetraazacyclododecane-1,4,7-triacetic acid and the salts thereof of formula (I)

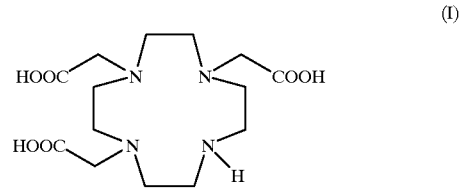

which comprises the following steps:

a) carboxymethylation reaction of a suitable precursor in water, with a haloacetic acid, b) hydrolysis reaction in basic conditions by addition of the base added at the previous step.

8 Claims, No Drawings

PROCESS FOR THE PREPARATION OF 1,4,7, 10-TETRAAZA-CYCLODODECANE-1,4,7-TRIACETIC ACID AND THE DERIVATIVE THEREOF

This is a division of application Ser. No. 09/095,016, filed Jun. 10, 1998, now U.S. Pat. No. 5,962,679.

1,4,7,10-Tetraazacyclododecane-1,4,7-triacetic acid (more commonly known as DO3A) of formula (I)

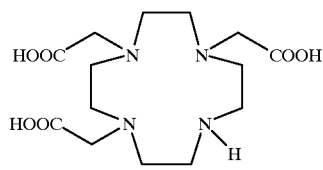

(I)

is the key intermediate for the synthesis of mono-N-substituted derivatives of formula (VIII),

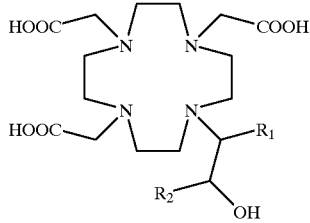

(VIII)

wherein $R_1$ and $R_2$ are independently a hydrogen atom, a ($C_1$–$C_{20}$) alkyl containing 1 to 10 oxygen atoms, or a phenyl, phenyloxy, phenyldioxy group, which is in its turn unsubstituted or substituted with a ($C_1$–$C_5$) alkyl or hydroxy, ($C_1$–$C_5$) alkoxy, carbamoyl or carboxylic groups.

Such compounds are used in particular for the synthesis of complexes with metal ions, specifically when the metals are paramagnetic, for the preparation of non-ionic contrast agents for the diagnostic technique known as magnetic resonance (MRI, Magnetic Resonance Imaging), among which are ProHance® Gadoteridol, gadolinium complex of 10-(2-hydroxypropyl)-1,4,7,10 -tetraazacyclododecane-1,4, 7-triacetic acid) and Gadobutrol (gadolinium complex of [10-[2,3-dihydroxy-1-(hydroxymethyl)propyl]-1,4,7,10-tetraazacyclododecane-1,4,7-triacetic acid).

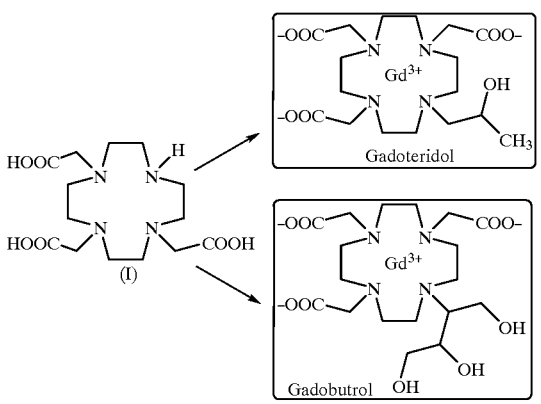

The synthesis of compound (I) was first described in EP 29,2689 and EP 232,751 and subsequently a paper was published (Dischino et al., Inorg. Chem., 1991, 30, 1265) which compared the possible synthetic routes with the most efficient one, which is that represented in Scheme 1, starting from 1,4,7,10-tetraazacyclododecane disulfate (II), a commercially available product.

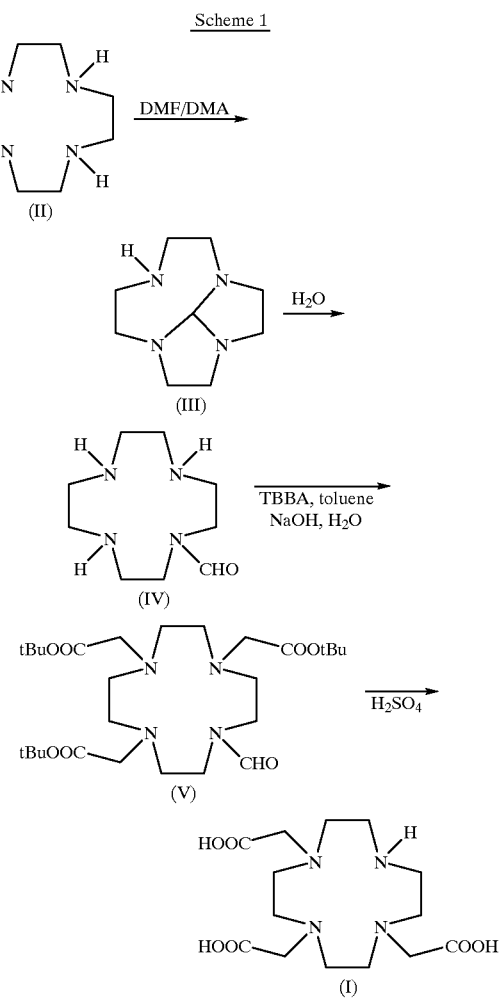

Scheme 1

The step from compound (II) to compound (III), 5H,9bH-2a,4a,7-octahydrotetraazacycloocta[cd]pentalene, is effected according to the conventional method described in US 4085106, followed by formation of 1-formyl-1,4,7,10-tetraazacyclododecane of formula (IV) in water-alcohol medium.

This intermediate is subsequently tricarboxymethylated in dimethylformamide at 2.5° C. with tert-butyl bromoacetate (TBBA), then treated with a diphasic toluene-sodium hydroxide mixture to give the compound of formula (V), 10-formyl-1,4,7,10-tetraazacyclododecane-1,4,7-triacetic acid, tris(1,1-dimethylethyl) ester, which is then hydrolysed to compound of formula (I) in acidic solution.

The industrialization of this synthesis involves a number of serious problems, in that:

the tert-butyl bromoacetate (TBBA) reactive is extremely toxic and very expensive;

dimethylformamide is harmful, teratogenic, and has a unnegligible cost;

the use of toluene involves risks of explosion due to electrostatic self-ignition;

the use of a mixture of two solvents (DMF and toluene) makes the recovery of both of them expensive;

the operative procedure is long and troublesome, obviously affecting the production costs, and involves many critical operations to a successful synthesis, therefore implying a remarkable cost of the process controls and/or the reduction of the chances of the success of the synthesis.

Moreover, during the hydrolysis step from compound (VI) to compound (I), gaseous isobutene is formed, which has necessarily to be absorbed due to environmental reasons.

Finally, notwithstanding the expensive experimental conditions, the selectivity of the carboxymethylation and hydrolysis reactions is not sufficient to obtain the compound of formula (I) at a high purity grade, thereby making it necessary a purification step of compound (I), for example by chromatography or by crystallization.

It is therefore evident that, to make an industrial production possible, the synthesis of compound (I) should be improved, reducing, when possible, the number of the synthetic steps and limiting the use of organic solvents and of reactives for the formation of the protective groups.

It has now surprisingly been found, and this is the object of the present invention, a process for the preparation of the compound of formula (I), which comprises the steps represented in Scheme 2:

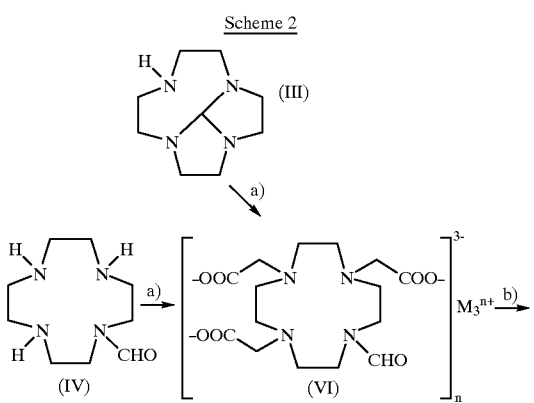

Scheme 2

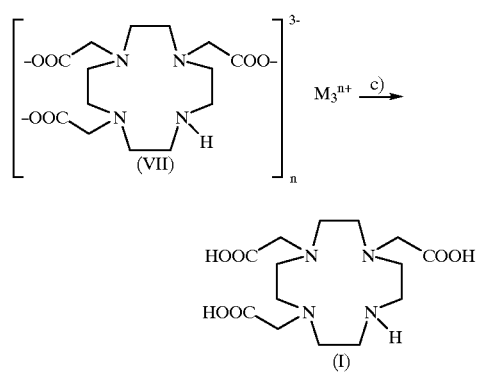

in which a) is the carboxymethylation reaction starting from (III) or (IV), in water, in molar ratios of haloacetic acid to compound (IV) or (III) ranging from 3 to 5 mol/mol, at pH ranging from 9.5 to 12.5 by addition of an alkali or alkaline-earth metal hydroxide, at a temperature from 7 to 50° C., for a time between 3 and 48h, to give the intermediate of formula (VI), 10-formyl-1,4,7,10-tetraazacyclododecane-1,4,7-triacetic acid salt with the metal cation corresponding to the used hydroxide, which, without being isolated, undergoes the hydrolysis reaction corresponding to step b);

b) is the hydrolysis reaction of the intermediate (VI) in basic conditions by addition of the same base as at step a), at a pH higher than 12.5, at a temperature ranging between 65° C. and 100° C. and for a time from 5 to 48 h, to give an aqueous solution of the salt of formula (VII), which, without being isolated, undergoes step c);

c) is the isolation step of compound (I), which is generally unnecessary and can be carried out, for example, by chromatographic steps on ion exchange resins.

A further object of the present invention are the novel compound, 10-formyl-1,4,7,10-tetraazacyclododecane-1,4,7-triacetic acid of formula (VIa), as well as the salts thereof with an alkali or alkaline-earth metal, of formula (VI),

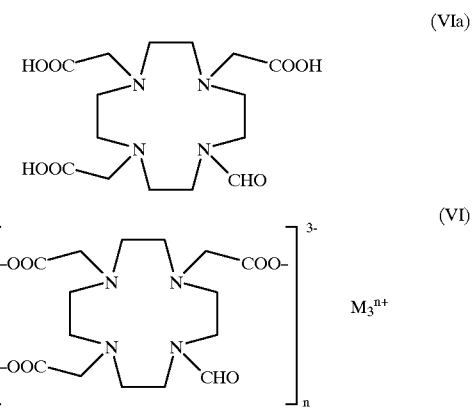

as intermediates in the process for the preparation of compound (I).

Particularly preferred are the salts of formula (VI), with sodium, potassium or calcium.

Particularly preferred is the use of bromoacetic acid and chloroacetic acid in the carboxymethylation step a).

The preferred conditions to carry out step a) are the following ones:

molar ratio of haloacetic acid to compound (III) or (IV) from 3.2 to 4.5;

pH from 10 to 12.

A further object of the present invention is the process for the preparation of 1,4,7,10-tetraazacyclododecane-1,4,7-triacetic acid (DO3A) mono-N-substituted derivatives of formula (VIII),

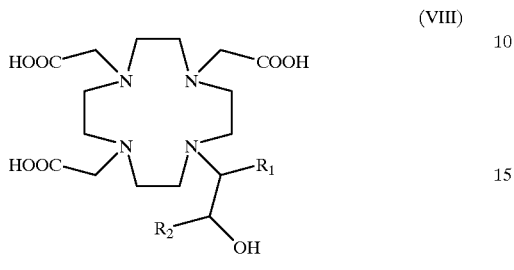

(VIII)

wherein $R_1$ and $R_2$ are independently a hydrogen atom, a $(C_1-C_{20})$ alkyl containing 1 to 10 oxygen atoms, or a phenyl, phenyloxy, phenyldioxy group, which is in its turn unsubstituted or substituted with a $(C_1-C_5)$ alkyl or hydroxy, $(C_1-C_5)$ alkoxy, carbamoyl or carboxylic groups, comprising the following steps represented in Scheme 3:

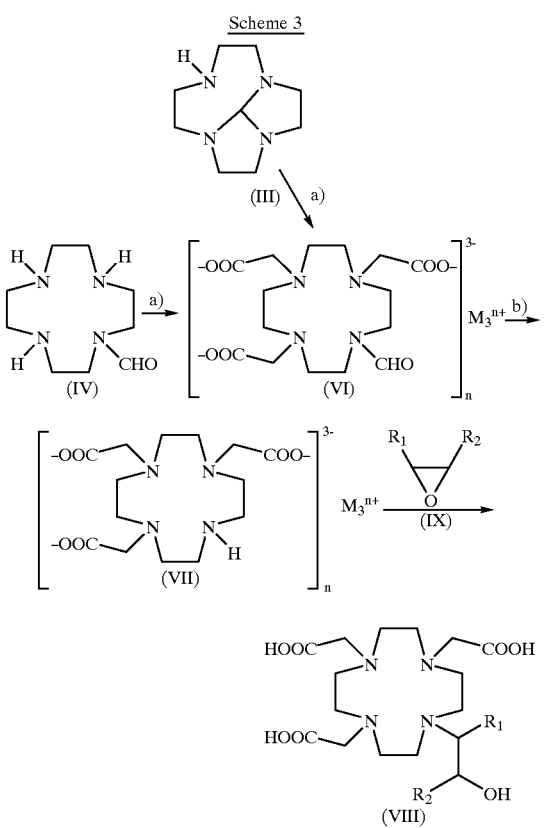

starting from compounds of formula (III) or (IV), through the formation of intermediate (VI) by means of the carboxymethylation reaction a), as defined above, and the subsequent hydrolysis b), as defined above, to give the alkaline aqueous solution of the alkali or alkaline-earth metal salt of compound (VII), which can be alkylated with an epoxide of formula (IX), in which $R_1$ and $R_2$ have the meanings defined above.

Particularly preferred is the preparation of 10-(2-hydroxypropyl)-1,4,7,10-tetraazacyclododecane-1,4,7-triacetic acid),

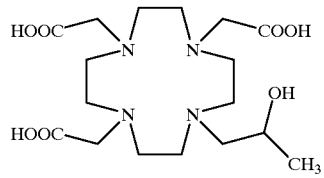

in which the epoxide of formula (IX) is propylene oxide, and the preparation of [10-[2,3-dihydroxy-1-(hydroxymethyl) propyl]-1,4,7,10-tetraazacyclododecane -1,4,7-triacetic acid),

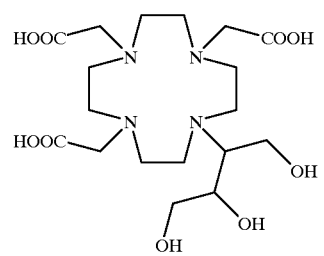

in which the epoxide of formula (IX) is 4,4-dimethyl -3,5,8-trioxabicyclo[5.1.0]octane.

Therefore, the process of the present invention makes it possible to carry out the carboxymethylation of compounds (IV) or (III) in aqueous solution, thus completely avoiding the use of undesired organic solvents.

More specifically, the carboxymethylation of (III) or (IV) in aqueous solution requires the use of a slight excess of a haloacetic acid, in the cited pH and temperature conditions.

The reaction yields a novel compound of formula (VI), acid 10-formyl-1,4,7,10-tetraazacyclododecane -1,4,7-triacetic acid, with a high selectivity, in aqueous alkaline solution which at the end of the reaction contains the haloacetic acid excess.

The confirmation of the structure of compound (VI) was carried out indirectly, due to its very high reactivity, by comparing the analytical data with those of the product resulting from the formylation reaction of compound (I), and it will be described in the Experimental section.

The deprotection of the formyl group in acidic medium, in the conditions already described in EP 292,689, can not be applied to the present process, in that the presence of a haloacetic acid excess would cause the conversion of compound (I) to DOTA as soon as pH is again made alkaline (for example, in an free-N alkylation step).

It is therefore a further object of the present invention the hydrolysis of (VI) in suitable basic conditions instead of in acidic conditions, so as to destroy the haloacetic acid excess before the deformylation of compound (VI).

The described conditions concerning carboxymethylation and hydrolysis make the process for the preparation of compound (I) dramatically easier.

Actually, as already mentioned, it is not even necessary to prepare intermediate (IV), in that its precursor, i.e. compound (III), can be used, thereby limiting the risk of hydrolysing the formyl group and, therefore, the need for controls of the process and production times, according to scheme 4.

Scheme 4

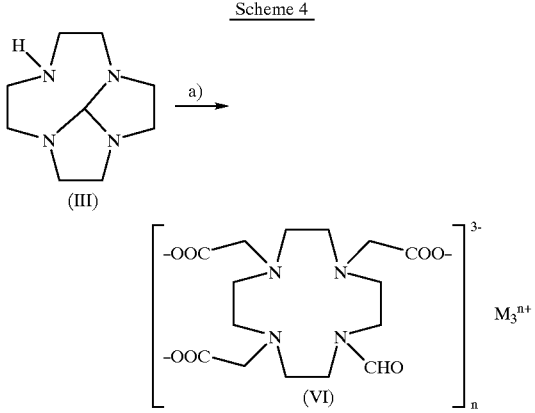

Compound (VI), therefore, is treated according to the reaction scheme already represented in Scheme 2.

The absence of gaseous by-products which are to be absorbed (such as isobutene) and of organic solvents, finally, are a further advantage of the process from the environmental and economic point of views.

One of the advantages provided by the process of the invention is that an aqueous solution of the compound of formula (I) is finally obtained, which can directly be used as such for the subsequent synthetic step, for the preparation of, for example, Gadobutrol and Gadoteridol.

As an example, in the case of the preparation of Gadoteridol, as described in EP 292,689, the alkaline aqueous solution of compound (I) is treated with propylene oxide to give, after the alkylation reaction, 10-(2-hydroxypropyl)-1,4,7,10-tetraazacyclododecane -1,4,7-triacetic acid (commonly known as HPDO3A), which is subsequently reacted with a gadolinium salt to obtain crude Gadoteridol.

The following examples illustrate the best experimental conditions to carry out the process of the invention.

The progress of the reactions is monitored by HPLC, using the following method:

Column: Polymer Labs PLRP-S 250×4 μm

Elution: isocratic

Mobile phase: A/B=99/1

A: 50 mM $NH_4H_2PO_4$ adjusted to pH 4 with 85% $H_3PO_4$

B: Methanol

Temperature: 30° C.

Detection: 270 nm

Flow: 0,5 mL/min

Preparation of the Sample

About 2 mg of product are placed in a 20 mL flask, then added with 0.5 ml of a solution of about 0.1 M $CuCl_2 \times 2H_2O$, derivatized for 15 min. at 35° C., then brought to volume with the eluent.

EXAMPLE 1

Preparation of Compound (I) using Bromoacetic Acid

A) Aqueous solution of compound (I)

A solution of 40 g (0.2 mol) of compound (IV) (prepared according to the procedure described in U.S. Pat. No. 4,085,106) in 150 ml of water is added with 122 g (0.70 mol) of a bromoacetic acid solution (80% w/w). The resulting pH 2 is adjusted to 11.3 by addition of 192 g of NaOH (30% w/w aqueous solution). The solution is heated to 45° C. The progress of the reaction is monitored by HPLC.

After 4h the conversion to compound (VI) is completed. 72 g of NaOH are added to pH 13, and the solution is heated at 80° C. for 6h, thereby obtaining a solution containing 67.8 g (0.196 mol) of the desired compound. Yield: 98% (HPLC assay in solution, as trisodium salt).

B) Isolation of compound (I) as sulfate

The solution from step A) is acidified with 192 g of 40% $H_2SO_4$ and added with acetone to precipitate 70.2 g of the desired compound (0.158 mol).

Yield: 81%

Alternatively, the solution from step A) is adjusted to pH 11 by addition of conc. HCl, then percolated on a column of sulfonic cation exchanger. After washing repeatedly with deionized water, the product is recovered by elution with 2N $NH_3$. The suitable fractions are concentrated in vacuum to a residue, which is redissolved in 240 ml of water and acidified with 60 g of conc. sulfuric acid. By gradual addition of acetone (total 250 mL), compound (I) precipitates as sulfate, which is recovered in an amount of 68.5 g (0.154 mol).

Yield: 79%

The $^1$H-NMR, $^{13}$C-NMR, IR and MS spectra are consistent with the indicated structure.

C) Free acid from the salt obtained at step B)

The salt from step B) is loaded onto a PVP resin (according to the procedure described in Dischino et al., Inorg. Chem., 1991, 30. 1265). 49.25 g of compound (I) are obtained (0.142 mol).

Yield: 90%

The $^1$H-NMR, $^{13}$C-NMR, IR and MS spectra are consistent with the indicated structure.

EXAMPLE 2

Preparation of Compound (I) using Chloroacetic Acid

A solution of compound (IV) (40 g. 0.2 mol) in 150 ml of water is added with 85 g (0.9 mol) of chloroacetic acid. pH is adjusted to 11.3 with NaOH and the mixture is reacted at a temperature of 40° C. for 48 h. pH is adjusted to 13 with NaOH, heating at 75° C. for 12 h. A solution containing 66.5 g of the desired compound as trisodium salt is obtained.

Yield: 96% (HPLC assay in solution)

EXAMPLE 3

Preparation of Compound (I) Starting from Compound (III)

100 g of water are added with 65.2 g of bromoacetic acid (0.47 mol) and 62.6 g of NaOH (30% w/w aqueous solution) to adjust pH to 5. The resulting solution is kept at 30° C. and added with 0.138 mol of compound (III), keeping pH at 10 by addition of NaOH. After that, pH is adjusted to 11.3 and kept at this value for 24 h, at the temperature of 30° C. Subsequently, 77.3 g of 30% NaOH (0.58 mol) are added, and the solution is heated at 75° C. for 9 h. A solution containing 58 g of the desired product as trisodium salt is obtained.

Yield: 97.5% (HPLC assay in solution)

EXAMPLE 4

Preparation of Compound (I) Ctarting from Compound (II) Without Recovery of the Intermediates 253.6 g of 1,4,7,10-tetraazacyclododecane of formula (II) (1.46 mol) containing 0.8% of water, are dissolved in 4350 g of toluene under nitrogen atmosphere. The mixture is heated at 110° C. and the toluene-water azeotrope is distilled off to a residual volume of 3.7 l. The solution is cooled to 60° C., 1.26 g of propionic acid are added, then 187.2 g (1.46 mol) of N,N-dimethylformamide dimethylacetal are dropped therein in 30 min. The toluene-water azeotrope is distilled off at a temperature of 90° C., then the solution is cooled to room temperature and added with 265 g of deionized water in 15 min. After 18 h stirring, the aqueous phase is separated and the organic phase is washed twice with total 835 g of deionized water. Washings are added to the aqueous phase and the resulting solution is added with 886 g of bromoacetic acid (80% in water, 5.11 mol). pH is adjusted to 11.3 with 30% w/w NaOH, added in 2 h, then the mixture is reacted at 45° C. for 4h. 520 g of 30% w/w NaOH are added, and the solution is heated at 80° C. for 16 h. An aqueous solution containing 455 g (1.31 mol) of DO3A, as trisodium salt, is obtained.

Yield: 90%

EXAMPLE 5
Preparation of Compound (III) and Immediate Conversion to 1,4,7,10-tetraazacyclododecane-1,4,7-triacetic Acid Usable for the Synthesis of Gadoteridol 110 g (0.634 mol) of 1,4,7,10-tetraazacyclododecane containing 0.7% w/w of water, are dissolved in 110 g of amyl alcohol. The water-amyl alcohol azeotrope and the amyl alcohol excess are distilled under reduced pressure, in succession, then 113 g (0.761 mol) of triethyl orthoformate and 1.2 g of propionic acid are added, in nitrogen atmosphere. The mixture is heated for 8 h at 135° C., while distilling the formed ethanol, then cooled to 35° C., to obtain compound (IV) as a fluid oil which is added to a solution prepared dissolving 274 g (1.972 mol) of bromoacetic acid and 263 g of 30% w/w NaOH in 370 g of water. During the addition of the crude compound (IV), pH is kept at 10 by addition of NaOH; afterwards pH is increased to 11.3, again by addition of 30% w/w NaOH, and the mixture is reacted for 24 h at 30° C. pH is adjusted to 13, and the solution is heated at 75° C. for 9 h. An aqueous solution containing 204 g (0.589 mol) of compound (I) (content determined by HPLC assay) as trisodium salt, is obtained. pH is adjusted to 12.3 with conc. HCl and 75 g (1.29 mol) of propylene oxide are added: after 3 h reaction at 35° C., the solution is cooled to 20° C., acidified to pH 1.5 with conc. HCl and reacted for 6 h in these temperature and pH conditions.

pH is adjusted again to 4.1 with conc. NaOH, then 121 g (0.334 mol) of gadolinium oxide are added. The slurry is heated at 98° C. for 5 h, then cooled, insolubles are filtered off and the solution is subjected to nanofiltration and, subsequently, to elution on a mixed bed of ion-exchange resins (strongly acidic cation-exchange resin and weakly basic anion-exchange resin). The suitable eluates, containing purified Gadoteridol, are concentrated to small volume and added while hot with isopropanol. The suspension is cooled to room temperature, then the crystallized solid is filtered.

298 g (0.482 mol) of Gadoteridol, containing 10% of hydration water, are obtained. Overall yield: 76%

The IR and MS spectra are consistent with the indicated structure.

EXAMPLE 6
Preparation of Compound (III) and Immediate Conversion to 1,4,7,10-tetraazacyclododecane-1,4,7-triacetic Acid (DO3A), Usable for the Synthesis of Gadoteridol A) Preparation of compound (III)

23.8 kg (0.138 kmol) of 1,4,7,10-tetraazacyclododecane containing 0.7% w/w of water, are dissolved in 23.8 kg of amyl alcohol. The water-amyl alcohol azeotrope and the amyl alcohol excess are distilled off at reduced pressure, in succession, then 24.5 kg (0.166 kmol) of triethyl orthoformate and 355 g of propionic acid are added, in nitrogen atmosphere. The mixture is heated for 11 h at 125° C., while distilling the formed ethanol, then cooled to 35° C., to obtain the compound (III) as a fluid oil.

B) Preparation of compound (VI)

Compound (III) from step A) is added to a solution prepared dissolving 81.5 kg (0.469 kmol) of bromoacetic acid and about 62.6 kg of 30% w/w NaOH in 100 kg of water to pH 5. During the addition of the crude compound (III), pH is kept at 11 by addition of NaOH; afterwards pH is increased to 11.1, again by addition of 30% w/w NaOH, and the mixture is reacted for 24 h at 35° C.

C) Preparation of compound (VII)

77.3 kg of 30% w/w NaOH are added and the mixture is heated to 70° C. for 9 h. An aqueous solution containing 0.131 kmol of compound (VII) (content determined by HPLC assay), as trisodium salt is obtained.

D) Synthesis of Gadoteridol pH is adjusted to 12.3 with conc. HCl and 15.2 kg (0.262 kmol) of propylene oxide are added. After 4 h reaction at 40° C., the solution is heated to 50° C. and added with 120 kg of an aqueous solution containing 0.135 kmol of gadolinium trichloride. After 1 h the solution is cooled to 17° C. and acidified to pH 1.7 with conc. HCl, and pH is controlled at this value for 2 h. Then the solution is heated to 50° C. and pH is adjusted to 7 with sodium hydroxide, and the solution is maintained at these conditions for 1 h.

E) Prepurification of the crude Gadoteridol solution

The crude Gadoteridol solution from the previous step is cooled and transferred through an in line filter and a column filled with 150 L of R&H Amberlite XAD 1600 resin, to a nanofiltration unit fitted with Desal DK4040F elements. When the reactor is empty, the reactor, the in line filter and the column are washed three times with 300 L of deionized water.

The resulting washing solution is combined with the product solution in the nanofiltration unit, where the product is concentrated and partially desalted at 32 bar and 25° C.

250 L of crude Gadoteridol solution with a conductivity of 2.9 mS/cm are obtained finally.

F) Final desalting

The Gadoteridol solution is then fed at 200 L/h to a series of 4 ion exchanger beds, the first (C1) consisting of 120 L of strongly basic anion exchanger Relite 3ASfb in the hydrogen carbonate form, the second (C2) consisting of 100 L of weakly acidic cation exchanger Relite CC in the $H^+$ form, the third (C3) consisting of 20 L of Relite 3ASfb in the $OH^{31}$ form and the fourth (C4) consisting of 20 L of Relite CC resin in the $H^+$ form. All the columns are ventead to the atmosphere and the liquid from the second column is passed through a gas separation tank, connected with a vacuum pump, to remove the evolved $CO_2$ from the solution. The outlet from the fourth column is fitted with a density transmitter to detect the product in the eluate. The first 180 L of eluate are discarded; the eluate is then collected in a product-rich fraction. When all the crude Gadoteridol solution has been loaded onto the ion exchange unit, the product is eluted with 600 L of deionized water, the eluate is then combined with the product-rich fraction, which is colourless and substantially free from ionic impurities (conductivity 2.2 $\mu$S/cm).

The yield of the final desalting, determined on the basis of the HPLC assay, is 98%.

G) Isolation of the product (Gadoteridol)

The product-rich fraction is then thermally concentrated to a viscous residue, which is added with 350 kg of isopropanol at 79° C. The resulting suspension is refluxed for 1 h, then cooled, centrifuged and dried at reduced pressure, to obtain 68.2 kg of Gadoteridol containing 10% of hydration water (0.111 kmol), HPLC assay 98.5% (s.a.). Overall yield: 80.7%

The IR and MS spectra are consistent with the indicated structure.

EXAMPLE 7
Preparation of 10-(2-hydroxypropyl)-1,4,7,10-tetraazacyclododecane-1,4,7-triacetic Acid Calcium Salt (Calteridol) Used as Stabilizer in the Gadoteridol Pharmaceutical Formulation ProHance®

100 g (0.225 mol) of compound (III), recovered as sulfate (prepared as described in example 1B) are dissolved in 100 ml of deionized water and treated with 27 g (0.458 mol) of propylene oxide at pH 12.3 by addition of 10N NaOH. After reacting for 3h at 40° C., the solution is acidified to pH 1.7 with conc. H$_2$SO$_4$, and it is kept at this pH for 1 h. After that, pH is adjusted to 3.8 with 10 N NaOH and the solution is concentrated under vacuum to 200 mL. 400 ml of methanol are added to the mixture, which is heated to 60° C. for 1 h, then cooled to room temperature, and the inorganic salts are filtered off and washed with methanol.

Methanol is distilled off from the filtrate, making up with water. The resulting solution is percolated on a bed of polyvynylpyridine resin.

The fractions containing the product are concentrated to 400 mL and treated with 68 g (0.676 mol) of CaCO$_3$. The mixture is refluxed for 90 min., cooled and the insoluble salts are filtered off. The filtrate is concentrated to 250 mL and added to 2 L of acetone.

After 2h at room temperature, the product is filtered, washing with acetone, then dried at 50° C. under vacuum to obtain 88 g (0.086 mol) of the desired product.

Yield: 76%

The $^1$H-NMR, $^{13}$C-NMR, IR and MS spectra are consistent with the indicated structure.

EXAMPLE 8

Preparation of Gadobutrol Starting From the Solution of Compound (I)

The aqueous solution of compound (I) at pH 13 obtained in Example 1 is reacted with 4,4-dimethyl -3,5,8-trioxabicyclo[5.1.0]octane according to the procedure described in WO9324469 to give the desired product.

The $^1$H-NMR, IR and MS spectra are consistent with the indicated structure.

EXAMPLE 9

Preparation 10-formyl-1,4,7,10-tetraazacyclododecane- 1,4,7-triacetic Acid

A 5-necked 1L flask fitted with mechanical stirrer, thermometer and reflux condenser is loaded with 35 g of compound (I), obtained as described in Example 1C, and 253 g of formic acid then, after keeping the resulting solution at 23° C. under mechanical stirring for 20 min., 74.6 g of acetic acid anhydride are then quickly added. The resulting solution is heated to 55° C. and kept at this temperature for 3 hours. After cooling to 23° C., 290 ml of abs. ethanol are dropped therein. The resulting solution is kept for three hours under magnetic stirring at a temperature of 23° C., then concentrated to an oily residue in a rotary evaporator.

The oily residue is dried in a static dryer in vacuum for 18 hours to obtain a waxy solid weighing 44.47 g, which is recrystallized from methanol and dried to obtain 25.7 g of the desired product.

The $^1$H-NMR, $^{13}$C-NMR, IR and MS spectra are consistent with the indicated structure.

We claim:

1. A process for the preparation of 1,4,7,10-tetraazacyclododecane-1,4,7-triacetic acid and the salts thereof, which comprises the steps according to the following scheme

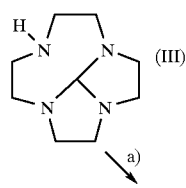

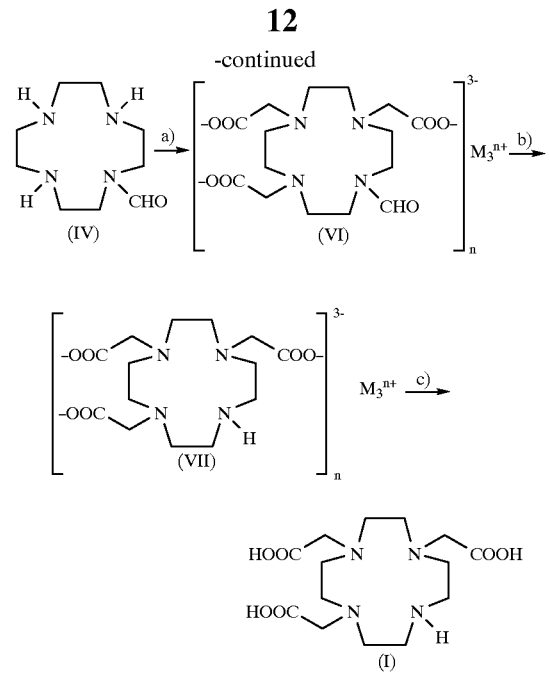

a) carboxymethylation reaction in basic conditions starting from compound (III) or from compound (IV), in water, with a haloacetic acid, to give intermediate (VI), which, without being isolated, undergoes the hydrolysis reaction described at the subsequent step b);

b) hydrolysis reaction of intermediate (VI) in basic conditions by addition of the same base as at step a), to give an aqueous solution of the salt of formula (VII), and which, without being isolated, can either be used as is or undergo subsequent c) recovery of compound (I).

2. A process as claimed in claim 1, wherein the intermediate of formula (VI) is a salt of a metal selected from: sodium, potassium and calcium.

3. A process according to claim 1, wherein said haloacetic acid is selected from bromoacetic acid and chloroacetic acid.

4. A process according to claim 1, wherein, in step a), the molar ratio of compound (III) or compound (IV) to haloacetic acid ranges from 3 to 5 mol/mol, pH is controlled in the range 9.5 to 12.5 by addition of an alkali or alkaline-earth metal hydroxide at a temperature from 7 to 50° C., for a time between 3 and 48 hours.

5. A process as claimed in claim 4, wherein said haloacetic acid is added in molar ratios from 3.2 to 4.5 to compound (III) or (IV) and pH ranges from 10 to 12.

6. A process for the preparation of compounds of formula (VIII),

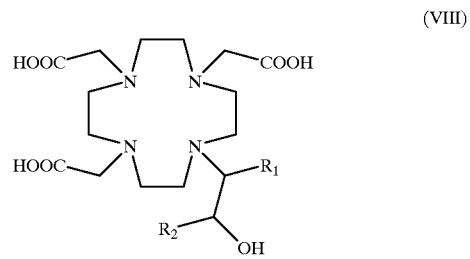

wherein
R$_1$ and R$_2$ are independently a hydrogen atom, a (C$_1$–C$_{20}$) alkyl containing 1 to 10 oxygen atoms, or a phenyl, phenyloxy, phenyldioxy group, which is in its turn unsubstituted or substituted with a $(C_1-C_5)$ alkyl or hydroxy, $(C_1-C_5)$ alkoxy, carbamoyl or carboxylic groups; which process comprises reacting at basic pH an aqueous solution of a compound of formula (VII) and an epoxide of formula (IX),

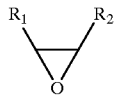
(IX)

wherein $R_1$ and $R_2$ have the meanings defined above.

7. A process as claimed in claim 6, wherein $R_1$ is hydrogen and $R_2$ is methyl.

8. A process as claimed in claim 6, wherein, in compound (VIII), $R_1$ and $R_2$ are hydroxymethyl and the epoxide of formula (IX) is 4,4-dimethyl-3,5,8-trioxabicyclo[5.1.0] octane.

* * * * *